United States Patent [19]

Shackelford et al.

[11] 4,426,540

[45] Jan. 17, 1984

[54] SYNTHESIS OF VINYL ETHERS

[75] Inventors: Scott A. Shackelford, USAF Academy, Colo.; Raymond R. McGuire, Brentwood, Calif.; Robert E. Cochoy, Dayton, Ohio

[73] Assignee: The United States of America as represented by the Secretary of the Air Force, Washington, D.C.

[21] Appl. No.: 694,261

[22] Filed: Jun. 10, 1976

[51] Int. Cl.$^3$ ............................................. C07C 43/00
[52] U.S. Cl. ................................... 568/590; 568/589; 149/19.3; 149/19.91; 149/88
[58] Field of Search ..................... 260/632 N; 149/88; 568/589, 590; 149/19.3, 19.9

[56] References Cited

U.S. PATENT DOCUMENTS 3,872,158  3/1975  Marcus .............................. 149/88 X

*Primary Examiner*—Stephen J. Lechert, Jr.
*Attorney, Agent, or Firm*—Donald J. Singer; Cedric H. Kuhn

[57] ABSTRACT

Vinyl ethers are prepared by reacting divinyl ether with a primary alcohol in the presence of a catalytic amount of red mercuric oxide and trifluoroacetic acid. The vinyl ethers so produced are particularly useful as monomers which can be polymerized into energetic macromolecular binder materials with excellent mechanical, physical and energetic properties.

8 Claims, No Drawings

SYNTHESIS OF VINYL ETHERS

RIGHTS OF THE GOVERNMENT

The invention described herein may be manufactured and used by or for the Government of the United States for all governmental purposes without the payment of any royalty.

FIELD OF THE INVENTION

This invention relates to a process for synthesizing energetic vinyl ether monomers.

BACKGROUND OF THE INVENTION

As disclosed in U.S. Pat. No. 2,808,182, 2,2-dinitroalkyl vinyl ethers are energetic monomers that can be used in the preparation of energetic organic polymers. The polymers can be used as ingredients in plastic-bonded explosive and propellant compositions.

According to the patent disclosure, the 2,2-dinitroalkyl vinyl ethers are prepared by contacting vinyl acetate with the corresponding 2,2-dinitroalkanol in the presence of $HgSO_4$ as catalyst at a temperature between $-5°$ and $5°$ C. As described in the examples, after a reaction period of 16 hours, a multi-step procedure is followed in isolating the vinyl ether product. For example, according to Example I, the reaction mixture was washed with two portions of aqueous sodium hydroxide and with water; the organic layer was dried over magnesium sulfate; excess vinyl acetate was removed under reduced pressure; the crude vinyl ether was distilled from the residual oil; the distillate was washed with two portions of sodium hydroxide and with water; and the organic layer was dried over magnesium sulfate and fractionated to give the vinyl ether product. There is a need for a simple one-step, high yield process for preparing energetic vinyl ethers under mild reaction conditions that does not involve a complicated procedure of product recovery.

It is a principal object of the present invention, therefore, to provide an improved process for preparing energetic vinyl ethers.

Another object of the invention is to provide a one-step, high yield process for preparing energetic vinyl ethers that is carried out under mild reaction conditions followed by a simplified product work-up procedure.

A further object of the invention is to provide a catalyst system for synthesizing vinyl ethers.

Other objects and advantages of the invention will become apparent to those skilled in the art upon consideration of the accompanying disclosure.

SUMMARY OF THE INVENTION

Broadly speaking, the present invention resides in a process for synthesizing energetic vinyl ether monomers which comprises the step of reacting divinyl ether with a primary alcohol in the presence of a catalytic amount of red mercuric oxide and trifluoroacetic acid.

In a more specific embodiment, equimolar amounts of divinyl ether and a primary alcohol having the formula

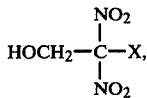

wherein X is fluorine, nitro or $(CH_2)_nCH_3$ and n is zero, 1 or 2, are reacted in a chlorinated hydrocarbon solvent in the presence of a catalytic amount of red mercuric oxide and trifluoroacetic acid. The reaction involved can be represented by the following equation:

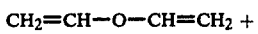

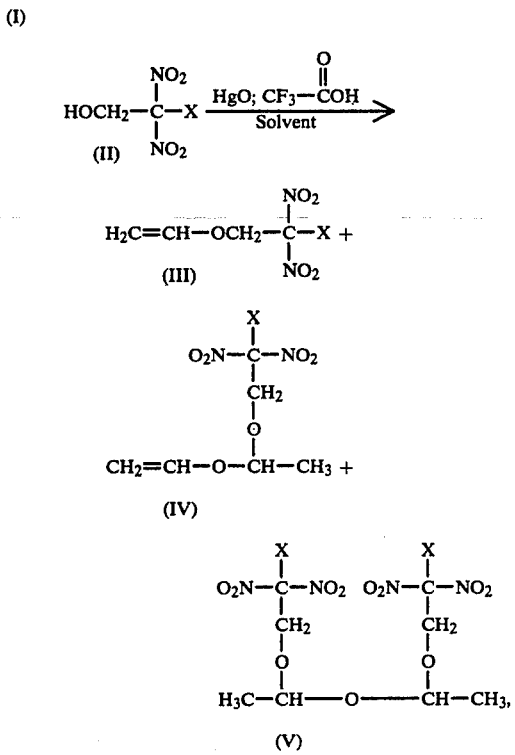

wherein X is fluorine, nitro or $(CH_2)_nCH_3$ and n is zero, 1 or 2.

The reaction represented by the foregoing equation is carried out in a chlorinated hydrocarbon solvent under reflux conditions and atmospheric pressure. The reaction time generally ranges from about 6 to 72 hours. Vinyl ether (III) is obtained in high yields, e.g., up to 70 percent and higher, as the product of the process. Trace amounts of side products (IV) and (V) may be present in the reaction mixture, but, if desired, they can be readily separated from the product, e.g., by vacuum distillation. However, the presence of the trace amounts of the side products does not generally have an adverse effect upon the utility of the vinyl ether product.

The primary alcohols employed in the present process display low nucleophilic character. Examples of primary alcohols that can be used include 2-fluoro-2,2-dinitroethanol, 2,2-dinitropropanol, 2,2-dinitrobutanol, 2,2-dinitropentanol, and 2,2,2-trinitroethanol. In general, the product yield varies according to the particular alcohol reactant selected. It is often preferred to employ 2,2-dinitropropanol.

Exemplary chlorinated hydrocarbons useful as solvents include methylene chloride, chloroform, carbon tetrachloride, 1,2-dichloroethane, and the like. It is usually preferred to employ methylene chloride.

In carrying out the process, equimolar amounts of the divinyl ether and primary alcohol are utilized. It is important to operate in this manner in order to obtain maximum yields with a minimum of side products. The amount of mercuric oxide used generally ranges from about 10 to 30 weight percent, based upon the weight of the divinyl ether. Stated in another manner, about 7 to 21 grams of mercuric oxide per mole of divinyl ether are used. The amount of trifluoroacetic acid usually ranges from about 0.7 to 2.1 milliliters per mole of divinyl ether.

At the end of the reaction period, the vinyl ether product is isolated as an oil by in vacuo solvent removal. The crude oil so obtained is readily purified by elution through a neutral alumina column with a chlorinated hydrocarbon solvent, such as carbon tetrachloride. The solvent is removed in vacuo, leaving a fairly pure vinyl ether product. If desired, the product can be vacuum distilled to provide an oily vinyl ether of analytical purity that is free of any trace amounts of side products (IV) and (V). The conditions used in the in vacuo removal of solvent and in the vacuum distillation will vary with the solvent used and the vinyl ether product prepared. However, it is well within the skill of the art to select appropriate conditions for these operations.

A more comprehensive understanding of the invention can be obtained by referring to the following illustrative examples which are not intended, however, to be unduly limitative of the invention.

EXAMPLE I

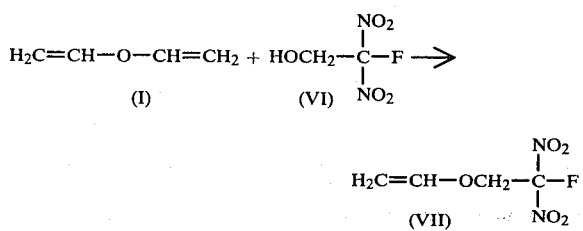

A 50 ml single necked, round bottom flask was charged with 20 ml of methylene chloride, 0.5 g (7.14 mmoles) divinyl ether (I), 1.1 g (7.14 mmoles) 2-fluoro-2,2-dinitroethanol, and 0.1 g red mercuric oxide. The solution was stirred with a Teflon coated magnetic bar while 100 μl trifluoroacetic acid was used. The reaction flask was then fitted with a water cooled reflux condenser and drying tube filled with Drierite desiccant. The reaction mixture was then stirred under reflux (~37° C.) for 22.5 hours. At the end of this period, the methylene chloride solvent was removed in vacuo, leaving a slightly yellow, clear oil. The oil was taken up in carbon tetrachloride and eluted with 35 ml carbon tetrachloride through 2.5 g neutral alumina (pH 7.3) packed in a 15 ml "course" glass sintered funnel. The carbon tetrachloride was removed in vacuo, leaving 0.94 g of colorless crude 2-fluoro-2,2-dinitroethyl vinyl ether (VII) which was shown by nuclear magnetic resonance spectrometry to be 84 percent pure.

The product obtained in a similar run was vacuum distilled at 34°-35° C. and 1 mm Hg or at 61°-62° C. and 13 mm Hg to provide compound (VII) of analytical purity. Nuclear magnetic resonance, infrared and mass spectrometry spectra of the distilled product were consistent with the structure of compound (VII).

Molecular Wt: Calc'd: 180.
Mass Spectrometry: 180.

EXAMPLE II

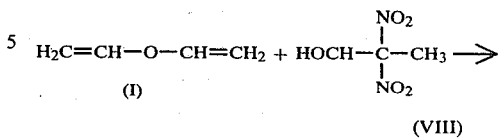

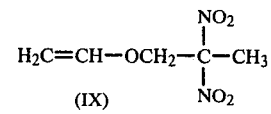

A 50 ml single necked, round bottom flask was charged with 20 ml methylene chloride, 0.50 g (7.14 mmole) divinyl ether, 1.07 g (7.14 mmole) 2,2-dinitropropanol (VIII), and 0.1 g red mercuric oxide. The solution was stirred, using a Teflon coated magnetic bar while 100 μl trifluoroacetic acid was added. The reaction flask was then fitted with a water cooled reflux condenser and drying tube filled with Drierite desiccant. The reaction was stirred under reflux (~37° C.) for 16 hours. The methylene chloride solvent was removed in vacuo, leaving a slightly yellow, clear oil. The oil was taken up in 2 ml carbon tetrachloride and placed onto 7.8 g neutral alumina (pH 6.9) packed with carbon tetrachloride into a 15 ml "course" glass sintered funnel. The carbon tetrachloride was removed in vacuo, leaving 0.74 g of crude 2,2-dinitropropyl vinyl ether (IX) which was shown by nuclear resonance spectrometry to be 92 percent pure.

The product obtained was vacuum distilled at 79°-81° C. and 1.5 mm Hg to provide compound (IX) of analytical purity. Nuclear magnetic resonance and infrared spectra of the distilled product were consistent with the structure of compound (IX). Elemental analysis of compound (IX) gave the following results:

Analysis (Wt%)-Calc'd for $C_5H_8N_2O_5$: C,34.09; H,4.54; N, 15.91; O,45.46. Found: C,33.83; H,4.70; N,16.03; O,45.44[(1)].

[(1)]Found by difference from C, H, N percentages.

EXAMPLE III

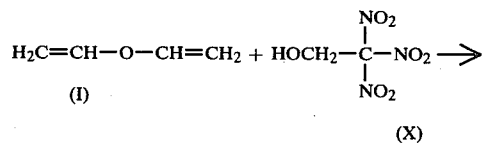

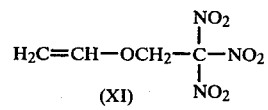

Following the procedure described in Examples I and II, divinyl ether and 2,2,2-trinitroethanol (X) were reacted for 60.25 hours in methylene chloride in the presence of red mercuric oxide and trifluoroacetic acid. A 25.9% yield of 2,2,2-trinitroethyl vinyl ether was obtained after elution with carbon tetrachloride through the neutral alumina (pH 7.3) column, followed by column chromatographic removal of 2,2,2-trinitroethanol in hexane through 60/200 mesh $SiO_2$.

The nuclear magnetic resonance spectrum was consistent with the structure of compound (XI).

As seen from the foregoing examples, the present invention provides a one-step process whereby vinyl ether compounds are synthesized in high yields under mild reaction conditions. At the end of the reaction period, the vinyl ether products are recovered by a simple work-up procedure.

The vinyl ethers are energetic monomers that can be polymerized into energetic macromolecular binder materials by well known processes that generate no volatile by-products. Such polymerization processes are very desirable since volatile by-products often degrade the mechanical and physical properties of macromolecular structures, rendering them unsuitable for binder applications in composite materials. The binder materials prepared by polymerizing the vinyl ethers have excellent mechanical, physical and energetic properties, and their inclusion into solid rocket propellants or explosive fills provide greater energy release in such volume-weight limited systems. This increased energy release provides longer range capabilities with solid propellant missiles and higher blast release from explosive devices.

As will be evident to those skilled in the art, modifications of the present invention can be made in view of the foregoing disclosure without departing from the spirit and scope of the invention.

We claim:

1. A process for preparing vinyl ethers which comprises reacting, under reflux conditions and atmospheric pressure for a period ranging from about 6 to 72 hours, equimolar amounts of divinyl ether and a primary alcohol having the following formula:

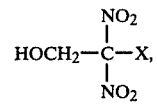

wherein X is fluorine, nitro or $(CH_2)_n CH_3$ and n is zero, 1 or 2, the reaction being conducted in a chlorinated hydrocarbon solvent in the presence of a catalytic amount of red mercuric oxide and trifluoroacetic acid.

2. The process according to claim 1 in which the amount of mercuric oxide ranges from about 10 to 30 weight percent, based upon the weight of the divinyl ether, and the amount of trifluoroacetic acid ranges from about 0.7 to 2.1 milliliters per mole of divinyl ether.

3. The process according to claim 2 in which the chlorinated hydrocarbon solvent is selected from the group consisting of methylene chloride, chloroform, carbon tetrachloride, and 1,2-dichloroethane.

4. The process according to claim 3 in which divinyl ether is reacted with 2-fluoro-2,2-dinitroethanol and 2-fluoro-2,2-dinitroethyl vinyl ether is recovered as the product of the process.

5. The process according to claim 3 in which divinyl ether is reacted with 2,2-dinitropropanol and 2,2-dinitropropyl vinyl ether is recovered as the product of the process.

6. The process according to claim 3 in which divinyl ether is reacted with 2,2,2-trinitroethanol and 2,2,2-trinitroethyl vinyl ether is recovered as the product of the process.

7. The process according to claim 3 in which divinyl ether is reacted with 2,2-dinitrobutanol and 2,2-dinitrobutyl vinyl ether is recovered as the product of the process.

8. The process according to claim 3 in which divinyl ether is reacted with 2,2-dinitropentanol and 2,2-dinitropentyl vinyl ether is recovered as the product of the process.

* * * * *